United States Patent
Cox

(10) Patent No.: US 7,906,766 B2
(45) Date of Patent: Mar. 15, 2011

(54) SYSTEMS AND METHODS FOR SIMULATING A VEHICLE EXHAUST PLUME

(75) Inventor: Philip Randall Cox, Madison, AL (US)

(73) Assignee: Northrop Grumman Systems Corporation, Los Angeles, CA (US)

( * ) Notice: Subject to any disclaimer, the term of this patent is extended or adjusted under 35 U.S.C. 154(b) by 178 days.

(21) Appl. No.: 12/139,831

(22) Filed: Jun. 16, 2008

(65) Prior Publication Data
US 2009/0309037 A1    Dec. 17, 2009

(51) Int. Cl.
*G01J 1/42* (2006.01)
(52) U.S. Cl. ......................................... 250/372
(58) Field of Classification Search ............... 250/372, 250/252.1, 504 R
See application file for complete search history.

(56) References Cited

U.S. PATENT DOCUMENTS

| | | |
|---|---|---|
| 4,173,777 A | 11/1979 | Schmit et al. |
| 5,523,579 A | 6/1996 | Orlando et al. |
| 7,026,756 B2 | 4/2006 | Shimizu et al. |
| 7,230,221 B2 | 6/2007 | Busse et al. |
| 2003/0035301 A1 | 2/2003 | Gardiner et al. |
| 2003/0053504 A1 | 3/2003 | Bour et al. |
| 2005/0247888 A1 | 11/2005 | Waluszko |
| 2005/0248299 A1 * | 11/2005 | Chemel et al. ............... 315/312 |
| 2005/0280785 A1 * | 12/2005 | Beeson et al. ................ 353/97 |
| 2006/0220046 A1 | 10/2006 | Yu et al. |
| 2006/0284050 A1 * | 12/2006 | Busse et al. ............... 250/203.1 |
| 2008/0164854 A1 * | 7/2008 | Lys ............................. 323/226 |
| 2008/0224025 A1 * | 9/2008 | Lyons et al. ................. 250/205 |
| 2008/0253118 A1 * | 10/2008 | Van As et al. ............... 362/237 |

OTHER PUBLICATIONS

Giza et al., "Ultraviolet scene simuation for missile approach warning system testing," 1997, Proceedings of SPIE, vol. 3084, pp. 282-291.*

International Search Report for corresponding PCT/US09/046817, mailed Mar. 3, 2010.

* cited by examiner

*Primary Examiner* — David P Porta
*Assistant Examiner* — Kiho Kim
(74) *Attorney, Agent, or Firm* — Tarolli, Sundheim, Covell & Tummino LLP

(57) ABSTRACT

A light emission system that comprises a light source that comprises at least one light emitting diode (LED) that provides ultraviolet light. The system also comprises a controller that controls the intensity of the ultraviolet light provided by the light source such that the ultraviolet light provided by the light source simulates a vehicle exhaust plume.

22 Claims, 5 Drawing Sheets

SYSTEMS AND METHODS FOR SIMULATING A VEHICLE EXHAUST PLUME

TECHNICAL FIELD

The present invention relates to light emissions and, more particularly, to systems and methods for simulating a vehicle exhaust plume of fuel propelled vehicles.

BACKGROUND

Fuel-propelled vehicles, such as rockets and missiles, utilize rocket motors to propel the vehicle through air and space. The rocket motors generally fall into three types, which are solid propellant motors, liquid propellant motors and hybrid propellant motors. Solid propellant motors utilize a solid fuel element or grain that is placed in a large solid combustion chamber. The solid fuel element or grain is usually bonded to the combustion chamber walls and burns away during flight. The liquid propellant motors employ liquid fuel tanks coupled to a fixed combustion chamber through one or more fuel lines. A hybrid propellant motor generally uses a fluid reactant (e.g., an oxidizer) to burn a solid fuel element or a fluid fuel element with a solid reactant, which are ignited in a combustion chamber. When the propellant is combusted, the resultant combustion reaction is typically propelled from one end of the fuel-propelled vehicle, and can be referred to as the vehicle exhaust plume. Typically, ultraviolet light is radiated from the vehicle exhaust plume.

Ultraviolet light detectors are utilized in rocket and missile defense systems. These ultraviolet light detectors can be mounted, for example, on an aircraft, or other vehicle that could be a target for one or more rockets and/or missiles. The rocket and missile defense systems employ optics and/or infrared technology to track rockets and/or missiles fired at or near the rocket and missile defense systems. The ultraviolet light detector can track rockets and/or missiles by detecting ultraviolet light provided by the plume of a rocket and/or missile. Typically, each type of rocket and/or missile has a different vehicle exhaust plume pattern, which can be referred to as the plume pattern. For instance, some missiles have longer effective ranges than others, thus requiring different rates of propellant combustion. Therefore, the intensity of the ultraviolet light provided by different types of missiles will be different. Additionally, the combustion of different forms of fuel (e.g., solid propellant, liquid propellant or hybrid propellant), can also provide different ultraviolet radiation patterns.

In one example, the detected intensity of the ultraviolet light provided by the rocket and/or missile can increase as the rocket and/or missile approaches the ultraviolet light detector. Additionally, when the rocket and/or missile is initially activated (e.g., fired), the ultraviolet light detector will typically detect a short pulse of increased intensity of ultraviolet light.

Obviously, it is not economically practical to test the detectors by firing live rockets and missiles. Therefore, plume simulators that provide ultraviolet light with a radiation pattern similar to the ultraviolet radiation pattern provided by the exhaust plume of rockets or missiles have been developed. The plume simulators typically employ at least one high power incandescent lamp to radiate the ultraviolet light needed to simulate an exhaust plume. Additionally, to simulate an initial burst of ultraviolet light, some plume simulators require the use of electromechanical shutters. However, incandescent lamps suffer from poor efficiency, a high failure rate and a relatively poor modulation rate, which make simulating a vehicle exhaust plume using incandescent lamps undesirable.

SUMMARY

One aspect of the present invention relates to a light emission system. The system comprises a light source that comprises at least one light emitting diode (LED) that provides ultraviolet light. The system also comprises a controller that controls the intensity of the ultraviolet light provided by the light source such that the ultraviolet light provided by the light source simulates an ultraviolet radiation pattern of a vehicle exhaust plume.

Another aspect of the present invention is related to a system for providing an ultraviolet light pattern. The system comprises means for providing ultraviolet light emitted from at least one LED. The system also comprises means for controlling the means for providing such that the ultraviolet light provided by the means for providing simulates an ultraviolet radiation pattern of a vehicle exhaust plume.

Yet another aspect of the present invention is related to a method of testing an ultraviolet light detector. The method comprises selecting a vehicle plume to be simulated. The method also comprises providing ultraviolet light to the detector from at least one LED that simulates an ultraviolet radiation pattern of the selected vehicle plume.

DETAILED DESCRIPTION

One or more ultraviolet light emitting diodes (LEDs) can be employed to simulate a vehicle exhaust plume of a vehicle, such as a rocket or a missile exhaust plume. The LEDs can provide ultraviolet light at a wavelength of about 255 nanometers to about 365 nanometers (nm). The LEDs could be formed, for example, from Gallium Nitride (GaN) and Aluminum Gallium Nitride (AlGaN). To simulate the vehicle exhaust plume, the intensity of the LEDs can be modulated in a predetermined manner to match the ultraviolet light pattern radiated by a rocket or missile plume. The simulated plume can be exposed, for example, to a detector. The detector can detect ultraviolet light radiated by the simulated plume and provide data that characterizes the detected ultraviolet light. The data provided by the detector can be analyzed, for example, to ensure that the detector is functioning properly.

Figure 1:
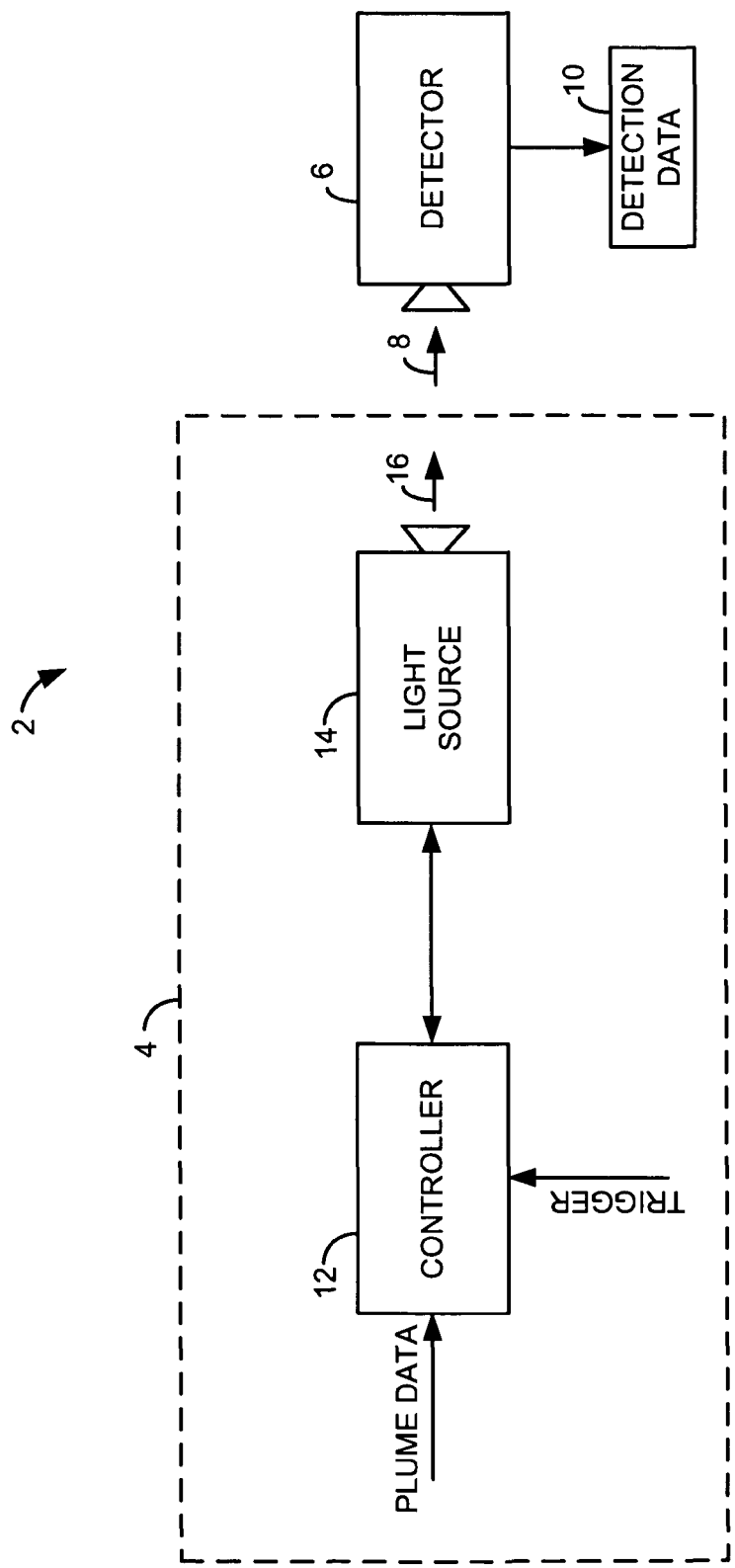
FIG. 1 depicts an example of a system for simulating a vehicle exhaust plume in accordance with an aspect of the invention.

FIG. 1 illustrates an example of a system 2 that can be used to simulate a vehicle exhaust plume, wherein the vehicle can be implemented, for example, as a rocket or missile. The system 2 includes a plume simulator 4 that provides an ultraviolet light to a detector 6. The detector 6 can detect the ultraviolet light provided at a direction indicated by the arrow at 8, and provide data that characterizes the detected ultraviolet light, which can be referred to as detection data 10, to a an external system (not shown). The external system could be implemented, for example, as hardware, software or a combination thereof, such as part of a missile defense system. The detector 6 could be implemented, for example, as a rocket and/or missile detector that could be mounted onto an aircraft. The detector 6 could include, for example, a photodetector that can detect ultraviolet light.

The plume simulator 4 can include a controller 12 coupled to a light source 14. The controller 12 could be implemented, for example, as hardware, software or a combination thereof. In one example, the controller 12 receives a PLUME DATA signal that characterizes a plume pattern. The plume pattern could correspond, for example, to an ultraviolet radiation pattern provided by a vehicle exhaust plume of a rocket or missile previously detected by the detector 6 (or a different detector). A typical plume pattern that could be provided to the controller 12 could include, for example, a short (e.g., 0.01 seconds) burst of relatively high intensity ultraviolet light, followed by a sharp decrease in the intensity of the ultraviolet light that is in turned followed by a gradual increase in intensity of the ultraviolet light. The short burst of relatively high intensity ultraviolet light could be implemented to simulate a missile fly out (e.g., the initial burst of light produced by a combustion reaction when a missile is fired at a target). The gradual increase of intensity of ultraviolet light could be used to simulate a rocket or missile moving closer and closer to the detector 6. As an example, the plume pattern could be executed in a time span of about 4-5 seconds. One skilled in the art will appreciate that other radiation patters and/or time spans could also be implemented.

A TRIGGER signal can be provided to the controller 12 that initiates the simulation of an ultraviolet radiation pattern of a vehicle exhaust plume. The TRIGGER signal could be provided, for example, by a button or an external system interface. The controller 12 causes the light source 14 to provide ultraviolet light at a pattern consistent with the plume pattern characterized by the PLUME DATA signal. The ultraviolet light could be provided in a direction indicated by the arrow at 16. The light source 14 can include, for example, one or more LEDs that can emit light at a wavelength of about 255 to about 365 nm. As one example, the LEDs could be formed from Gallium Nitride (GaN) and Aluminum Gallium Nitride (AlGaN).

In one example, the plume simulator 4 and the detector 6 could be placed about 1 to about 3 kilometers apart. The plume simulator 4 could be mounted, for example, on a tripod. The detector 6 could be mounted at an elevated position, such as on a rod or pole. Such an implementation can accurately simulate a rocket propelled grenade (RPG) being fired at an aircraft, such as a helicopter or a jet powered aircraft. Alternatively, the detector 6 could be mounted on a moving vehicle, such as a helicopter or jet powered aircraft. One skilled in the art will appreciate the various positions in which the plume simulator 4 and/or the detector 6 could be placed.

When the plume simulator 4 and the detector 6 are positioned correctly, the plume simulator 4 can provide a simulated ultraviolet radiation pattern of a vehicle exhaust plume in the direction indicated by the arrow at 16, a portion of which can be detected by the detector 6 in the direction indicated by the arrow at 8. The detector 6 provides the detection data 10 that characterizes the simulated plume to the external system. The external system can examine the detection data 10 to ensure that the detector 6 is functioning properly.

Figure 2:
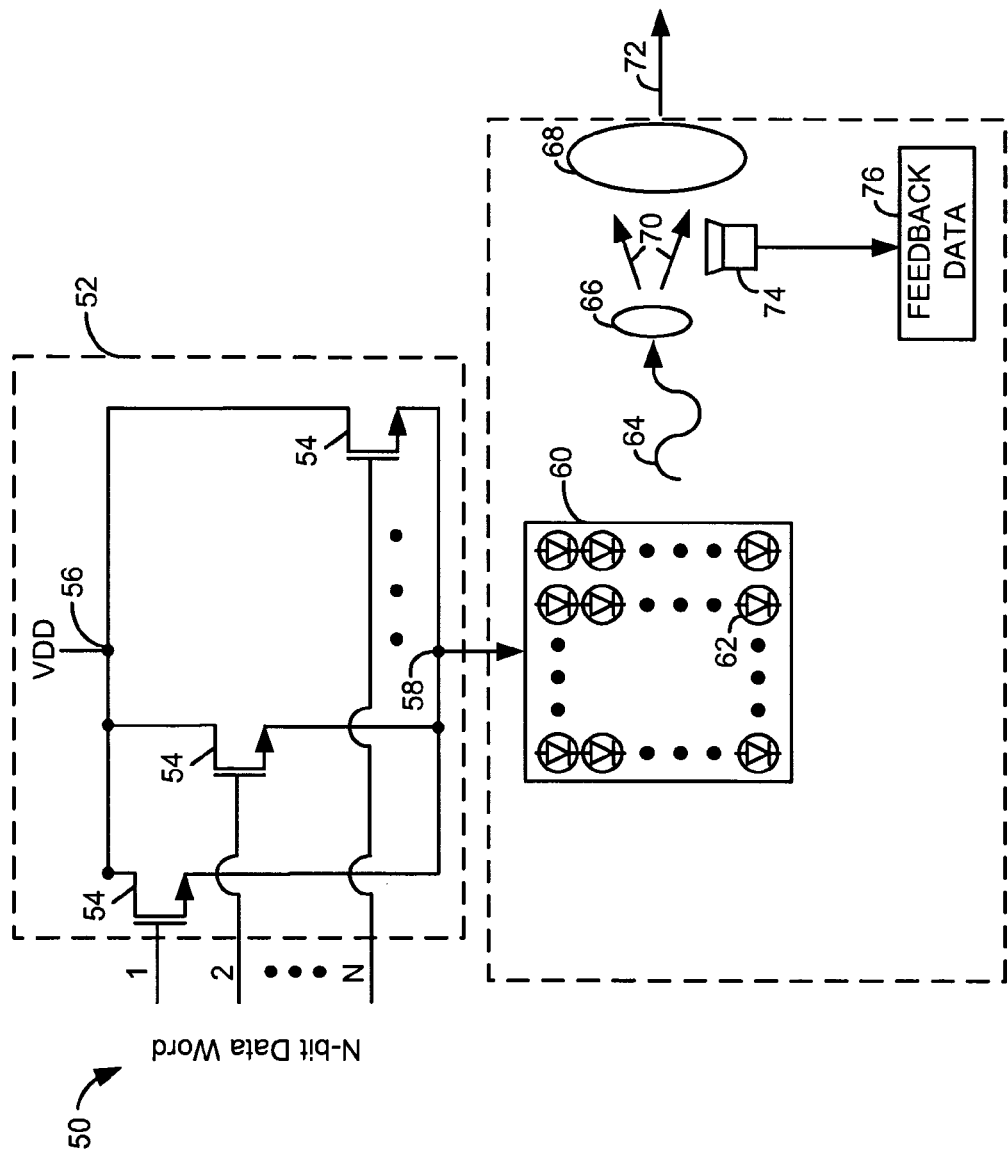
FIG. 2 depicts an example of a light source in accordance with an aspect of the invention.

FIG. 2 illustrates an example of a light source 50 that could be employed in a plume simulator in accordance with an aspect of the invention. The light source 50 can include a variable current source 52 (hereinafter, "VCS") coupled to an optical system 59. The VCS 52 could be implemented as a binary array of metal oxide semiconductor field effect transistors (MOSFETs) 54. The VCS 52 could be controlled, for example, by an N-bit data word provided by a controller, such as a microprocessor, where N is an integer greater than or equal to 1. As an example, the N-bit word could be implemented as a 16-bit word. In such an example, the array of MOSFETs 54 can be implemented as N number of transistors, such as MOSFETs 54, where each bit of the N-bit data word is provided to a gate of the corresponding MOSFET 54. The drains of each of the N MOSFETs 54 can be connected to a first common node 56 that provides a voltage of VDD, where VDD can be implemented, for example, as 5.5 volts (V) or other appropriate voltage. Each source of the N MOSFETs 54 can be connected to a second common node 58 that can provide an output current. Each of the N MOSFETs 54 can source current commensurate with the significance of the corresponding bit that controls a given MOSFET 54. That is, the Nth MOSFET 54 can source double the current that the N−1 MOSFET 54 can source, and the N−1 MOSFET 54 can source double the current that the N−2 MOSFET 52 can source, etc. Such an arrangement allows for precise control of the current provided by the VCS 52.

The current provided by the VCS 52 can be provided to the optical system 59, and more specifically to a J×K LED array 60, where J and K are integers greater than or equal to one. As one example, the J×K LED array 60 could be implemented as a 3×3 LED array. Each of the LEDs 62 can provide ultraviolet light at a wavelength at or near the ultraviolet electromagnetic waveband, such as about 255 nm to about 365 nm. As one example, the LEDs 62 could be formed from Gallium Nitride (GaN) and Aluminum Gallium Nitride (AlGaN). The light provided by the J×K LED array 60 can be provided in a direction indicated by an arrow at 64 to a coupling lens 66. The coupling lens 66 can combine the light provided by each of the LEDs 62 in the J×K LED array 60 and provided the combined light to a projection lens 68 in a direction indicated by the arrows at 70. The projection lens 68 can provide a projection beam at a predetermined projection radius, such as about 6 degrees. The projection beam can be provided in a direction indicated by an arrow indicated at 72.

A feedback detector 74 can be included to detect the intensity of the combined light. The feedback detector can include, for example, a photodetector that can detect ultraviolet light at a wavelength of about 255 nm to about 365 nm. The feedback detector 74 can provide feedback data 76, for example, to the controller. The feedback data 76 can be analyzed to ensure that the plume simulator is functioning properly and/or to adjust the intensity of the ultraviolet light provided by the light source 50.

Figure 3:
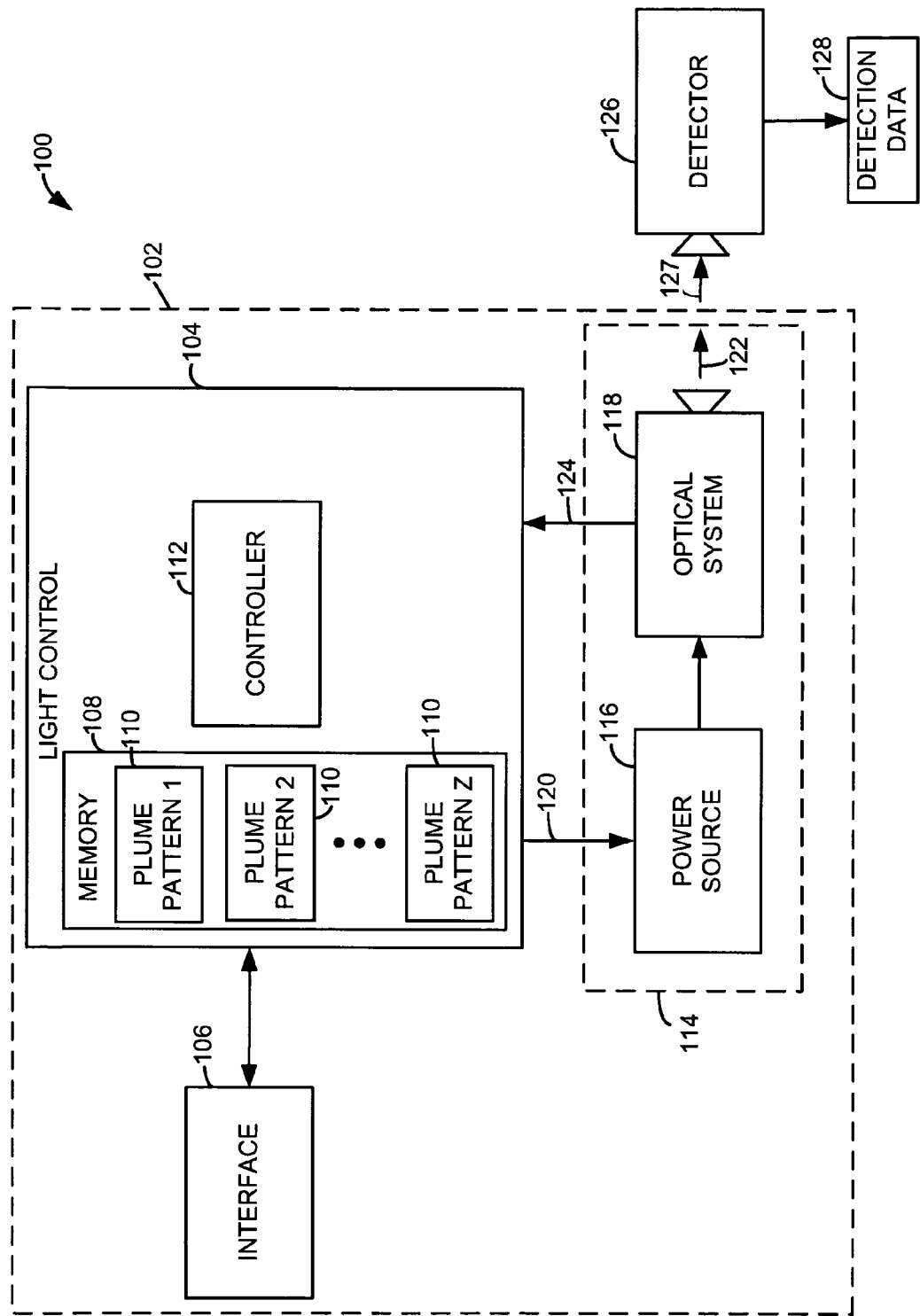
FIG. 3 depicts another example of a system for simulating a vehicle exhaust plume in accordance with an aspect of the invention.

FIG. 3 illustrates another example of a system 100 that includes a plume simulator 102 in accordance with an aspect of the invention. The plume simulator 102 includes a light control 104 that can be controlled by an interface 106. The interface 106 could be implemented, for example, as hardware, software or a combination thereof. As an example, the interface 106 can be controlled by a user, or the interface 106 can be autonomous. The light control 104 can be implemented as hardware, software or a combination thereof. The light control 104 includes a memory 108 that stores M number of plume patterns 110, where M is an integer greater than or equal to one. Additionally or alternatively, the plume patterns 110 can be provided by the interface 106. Each plume pattern 110 can, for example, include data that characterizes a particular vehicle exhaust plume pattern.

As an example, the user of the interface 106 can select a plume pattern 110, and cause the memory 108 to provide a controller 112 with the selected plume pattern 110. The controller 112 can cause a light source 114 to provide ultraviolet light that simulates the selected plume pattern 110. The light source 114 could be implemented, for example, as a power source 116 and an optical system 118 (e.g., see FIG. 2). The power source 116 could be implemented as a VCS. Alternatively, the power source 116 could be implemented as a variable voltage source. The power source 116 could be controlled, for example, by a digital signal 120 provided by the light control 104. In such a situation, the light control 104 can cause the power source 116 to provide the optical system 118 with a specific current.

The optical system 118 can include one or more LEDs (such as an LED array) that provide ultraviolet light at a wavelength from about 255 nm to about 365 nm. As one example, the one or more LEDs could be formed from Gallium Nitride (GaN) and Aluminum Gallium Nitride (AlGaN). The optical system 118 can provide the ultraviolet light at a direction indicated by the arrow indicated at 122. Additionally, the optical system 118 can provide a feedback signal 124 to the controller 112. The feedback signal 124 can, for example, characterize a detected intensity level of ultraviolet light provided by the optical system 118. The controller 112 can analyze the feedback signal 124 to ensure that the optical system 118 is outputting ultraviolet light at a correct level for a given point in time. If the feedback signal 124 indicates that the optical system 118 is outputting ultraviolet light at a level other than the correct level for the given point in time, the controller 112 can cause the power source 116 to increase or decrease the current provided to the optical system 118 to increase or decrease the intensity of the ultraviolet light provided by the optical system 118.

A detector 126 receives at least a portion of the light provided by the optical system 118 at a direction indicated by the arrow at 127. The detector 126 could be implemented, for example, as a photodetector that could be mounted in a vehicle, such as an aircraft. As an example, the detector 126 and the light source 114 can be separated by a distance of about 1 to about 3 kilometers. The detector 126 detects at least a portion of the ultraviolet light provided by the optical system 118. In response to detecting at least a portion of the ultraviolet light, the detector 126 can provide detection data 128 that characterizes the detected ultraviolet light. The detection data 128 could be provided to an external system, such as a spectrum analyzer, a missile defense system, or the detection data 128 can be stored in a memory, such as random access memory (RAM). The detection data 128 can be analyzed to ensure that the detector 126 is functioning properly.

Figure 4:
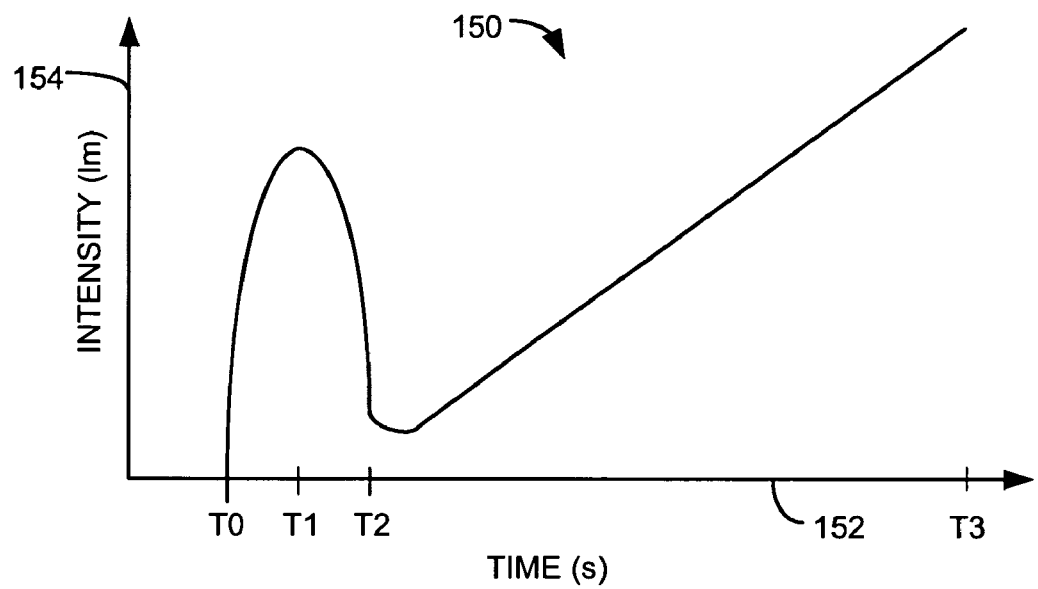
FIG. 4 depicts an example of an intensity pattern of ultraviolet light in accordance with an aspect of the invention.

FIG. 4 illustrates an example of a graph 150 of an ultraviolet light radiation pattern that could be implemented to simulate a vehicle exhaust plume of a vehicle (e.g., a plume pattern) in accordance with an aspect of the invention. The ultraviolet light pattern could be provided, for example, by the optical system 118 of the plume simulator 102 illustrated in FIG. 3. In FIG. 4, the horizontal axis 152 of the graph 150 can be measured in units of time, such as seconds(s). The vertical axis 154 can be measured in units of light intensity, such as lumens (lm). It is to be understood that the graph 150 is not drawn to scale, and that some parts of the graph have been exaggerated for purposes of simplification of explanation.

In the graph 150, at time T0, an initiation signal, such as a trigger signal can be activated by the interface 106 of the plume simulator 102. Shortly after the initiation signal, the light control 104 causes the light source 114 to sharply increase the intensity of the ultraviolet light provided. After a small period of time (e.g., about 0.01 seconds), the light control 104 causes the light source 114 to sharply drop the intensity of the light provided by the optical system 118 (e.g., at T1). This short burst of high intensity ultraviolet light can be employed to simulate a missile fly out. After the short burst of ultraviolet light, at a time T2, the intensity of the ultraviolet light will gradually increase at a substantially linear rate until another time, T3, such as about 4-5 seconds. This gradual increase simulates the intensity of ultraviolet light emitted from the exhaust plume of a rocket or missile as the rocket or missile approaches the detector 126.

Figure 5:
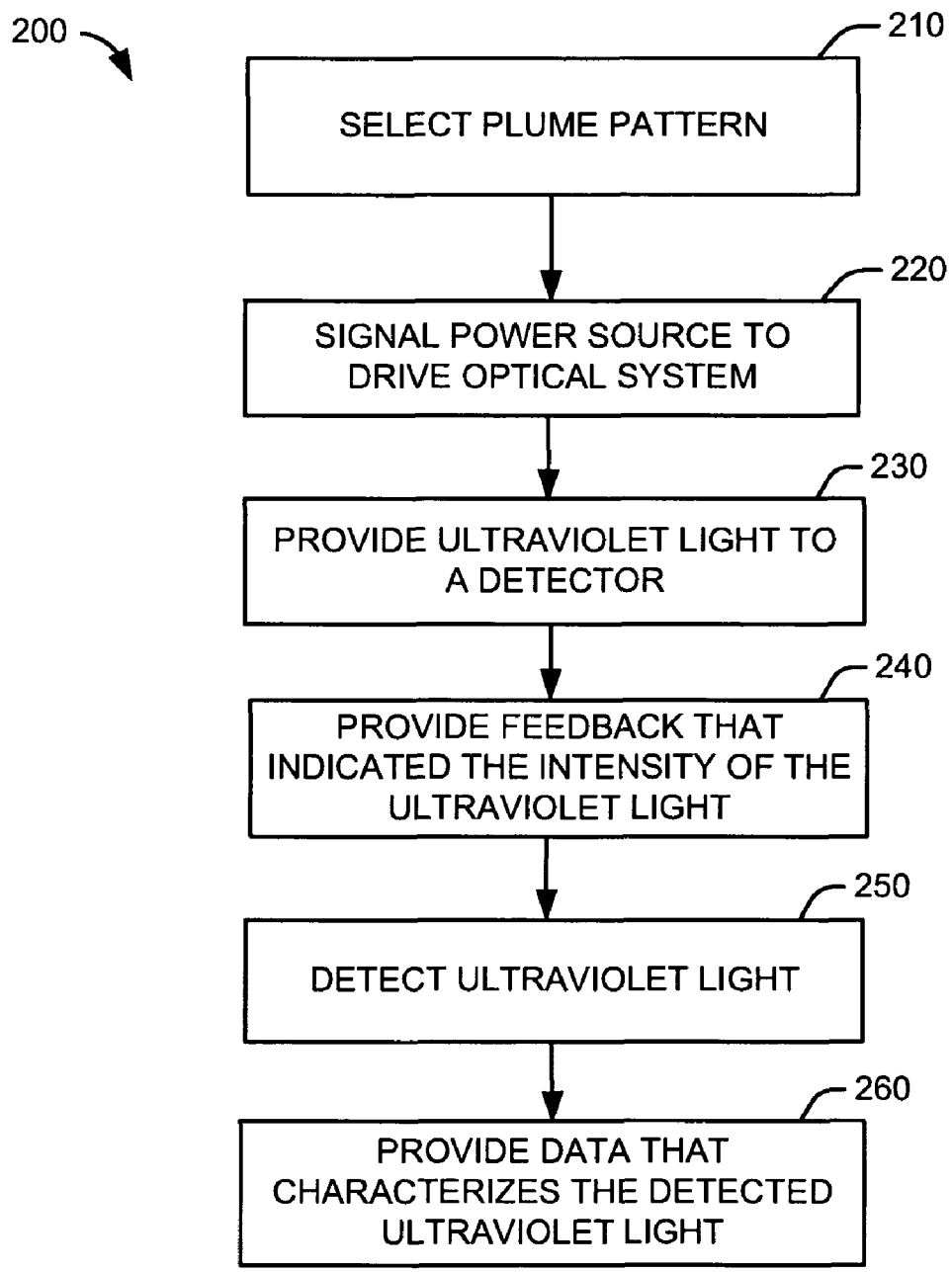
FIG. 5 depicts an example of method for testing an ultraviolet light detector in accordance with an aspect of the invention.

FIG. 5 illustrates a flowchart for a process 200 of testing an ultraviolet light detector. It is to be understood and appreciated that the illustrated actions, in other embodiments, may occur in different orders and/or concurrently with other actions. Moreover, not all illustrated features may be required to implement a process. At 210, a plume pattern is selected. The plume pattern can be selected, for example, by an interface that is controllable by a user. The plume pattern can correspond to an ultraviolet radiation pattern of a vehicle exhaust plume. The process proceeds to 220. At 220, a controller signals a power source to drive an optical system to produce an ultraviolet light pattern that simulates the selected plume. The optical system can include, for example, one or more LEDs that can produce light at a wavelength of about 255 nm to about 365 nm. The process proceeds to 230.

At 230, ultraviolet light is provided to a detector with a patter determined by the controller. The detector can be separated from the optical system by about 1 to about 3 kilometers away from the optical system providing the ultraviolet light. The process proceeds to 240. At 240, a feedback signal is provided to the controller. The feedback signal characterizes the intensity of the ultraviolet light provided by the optical system at a given point in time. The controller can utilize the feedback signal to determine if an adjustment of the intensity of the ultraviolet light provided by the optical system is necessary. The process proceeds to 250.

At 250, the detector detects at least a portion of the ultraviolet light provided by the optical system. The process proceeds to 260. At 260 the detector provides data that characterizes the ultraviolet light detected by the detector. The provided data can be stored and/or analyzed by an external system to determine if the detector is functioning properly.

What has been described above includes exemplary implementations of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A light emission system comprising:
   a light source that comprises at least one light emitting diode (LED) that provides ultraviolet light; and
   a controller that controls the intensity of the ultraviolet light provided by the light source such that the ultraviolet light provided by the light source simulates an ultraviolet radiation pattern of a vehicle exhaust plume.

2. The system of claim 1, wherein the at least one LED comprises an LED array.

3. The system of claim 2, wherein the light source further comprises:
   an optical system that houses the LED array; and
   a variable power source that drives the LED array of the optical system.

4. The system of claim 3, wherein the variable power source comprises a variable current source that is controllable by a data word provided by the controller.

5. The system of claim 3, wherein the optical system further comprises:
   a coupling lens that couples ultraviolet light provided by the LED array; and
   a projection lens that focuses the ultraviolet light at a predetermined projection angle.

6. The system of claim 3, wherein the optical system provides a feedback signal to the controller that characterizes an intensity of ultraviolet light provided by the LED array.

7. The system of claim 1, wherein the at least one LED is formed of Gallium Nitride and Aluminum Gallium Nitride.

8. The system of claim 1, wherein the at least one LED provides ultraviolet light within a band of light between about 255 nanometers to about 365 nanometers.

9. The system of claim 1, wherein the system further comprises a detector that detects at least a portion of the ultraviolet light provided by the light source, and provides data that characterizes the detected ultraviolet light.

10. The system of claim 9, wherein the light source and the detector are separated by at least 1 kilometer.

11. The system of claim 1, wherein the controller comprises a memory bank that stores a plurality of different plume patterns corresponding to a plurality of different ultraviolet radiation patterns of vehicle exhaust plumes.

12. The system of claim 11, further comprising an interface that selects one of the plurality of plume patterns.

13. A system for providing an ultraviolet light pattern, the system comprising:
   means for providing ultraviolet light emitted from at least one light emitting diode (LED); and
   means for controlling the means for providing such that the ultraviolet light provided by the means for providing simulates a radiation pattern of a vehicle exhaust plume.

14. The system of claim 13, further comprising means for detecting an intensity of the ultraviolet light provided by the means for providing.

15. The system of claim 14, wherein the means for detecting further comprises means for characterizing the detected ultraviolet light.

16. The system of claim 13, wherein the means for controlling further comprises means for driving the means for providing.

17. The system of claim 13, wherein the ultraviolet light provided by the means for providing is provided at a wavelength from about 255 nanometers to about 365 nanometers.

18. The system of claim 13, wherein the means for providing further comprises means for providing a feedback signal that characterizes the intensity of the ultraviolet light provided by the means for providing.

19. The system of claim 18, wherein the means for controlling is configured to adjust the intensity of the ultraviolet light provided by the means for providing based on the feedback signal.

20. A method of testing an ultraviolet light detector, the method comprising:
   selecting a vehicle exhaust plume to be simulated;
   providing ultraviolet light to the detector from at least one light emitting diode (LED) that simulates a radiation pattern of the selected vehicle exhaust plume.

21. The method of claim 20, further comprising detecting at least a portion of the ultraviolet light at a detector and providing data that characterizes the detected ultraviolet light.

22. The method of claim 20, further comprising:
   detecting an intensity of the ultraviolet light provided by the at least one LED; and providing a feedback signal that characterizes the intensity of the ultraviolet light.

* * * * *